United States Patent [19]

Heiba et al.

[11] 4,175,089

[45] Nov. 20, 1979

[54] PREPARATION OF GAMMA-BUTYROLACTONES

[75] Inventors: El Ahmadi I. Heiba, Princeton; Ralph M. Dessau, Highland Park, both of N.J.

[73] Assignee: Mobil Oil Corporation, New York, N.Y.

[21] Appl. No.: 336,857

[22] Filed: Feb. 28, 1973

Related U.S. Application Data

[63] Continuation-in-part of Ser. No. 30,582, Apr. 21, 1970, abandoned, which is a continuation-in-part of Ser. No. 714,447, Mar. 20, 1968, abandoned.

[51] Int. Cl.$^2$ .................. C07D 307/32; C07D 307/83; C07D 307/93
[52] U.S. Cl. ............................ 260/343.6; 260/343.3 R
[58] Field of Search ...................... 260/343.6, 343.3 R

[56] References Cited

U.S. PATENT DOCUMENTS

| | | | |
|---|---|---|---|
| 2,476,668 | 7/1949 | Kharasch et al. | 260/343.6 |
| 2,986,568 | 5/1961 | Johnston | 260/343.6 |
| 3,470,219 | 9/1969 | Hobbs et al. | 260/413 |

FOREIGN PATENT DOCUMENTS

1902329 11/1969 Fed. Rep. of Germany ........ 260/343.6

OTHER PUBLICATIONS

R. E. van der Ploeg, Aromatische Substitutie Door Middel Van Marganiacetat in Ijsazijn, Sep. 27, 1967, Phd. Thesis, University of Leiden.
R. E. van der Ploeg et al., *Journal of Catalysis*, vol. 10, 52–59 (1968).
Bush et al., *JACS*, Oct. 1968, pp. 5903–5905.
Heiba et al., *JACS*, Oct. 1968, pp. 5905–5906.
Chemical Abstracts, vol. 72, 1970, 78456j relied on.

*Primary Examiner*—Norma S. Milestone
*Attorney, Agent, or Firm*—Charles A. Huggett; Vincent J. Frilette

[57] ABSTRACT

Gamma-butyrolactones are formed by reacting an olefin with a compound containing a carboxylate moiety having at least one hydrogen atom on the alpha carbon atom in the presence of an ion of manganese, cerium, or vanadium, the ion being in a valency state higher than its lowest valency state.

14 Claims, No Drawings

PREPARATION OF GAMMA-BUTYROLACTONES

CROSS REFERENCE TO RELATED APPLICATIONS

This application is a continuation-in-part of our copending application Ser. No. 30,582, filed Apr. 21, 1970 now abandoned. The latter application is a continuation-in-part of our application Ser. No. 714,447, filed Mar. 20, 1968, which application was pending at the time application Ser. No. 30,582 was filed but which has since been abandoned.

BACKGROUND OF THE INVENTION

1. Field of the Invention

This invention relates to a process for the production of gamma-butyrolactones.

2. Description of the Prior Art

U.S. Pat. No. 2,569,064 discloses the preparation of gamma lactones by heating a 2,2,4-trihalogenoalkanoic ester in the presence of a catalytic amount of a metal halide including zinc chloride, boron trifluoride, antimony pentachloride, stannic chloride, and ferric chloride.

U.S. Pat. No. 2,968,568 discloses the preparation of butyrolactones by reacting bromoacetic acid and derivatives of the carboxylic group thereof with alpha olefins and with a catalyst. Catalysts which produce free radicals under the reaction conditions and polymerization catalysts are preferred. Catalysts disclosed are peroxides such as cumene hydroperoxide, acetyl peroxide, propionyl peroxide, lauroyl peroxide, benzoyl peroxide, benzoyl hydroperoxide and hydrogen peroxide. Other catalysts include perborates, percarbonates, persulfates, tetraethyllead, hydrazines, substituted hydrazines and their salts, and amine oxides such as triethyl amine oxide. Other means for producing free radicals which can be employed include ultraviolet light with or without chemical photosensitizers.

SUMMARY OF THE INVENTION

Gamma-butyrolactones are produced by reacting an olefin with a compound containing a carboxylate moiety having at least one carbon atom on the alpha carbon atom in the presence of an ion of manganese, cerium, or vanadium, the ion being in a valency state higher than its lowest valency state.

DESCRIPTION OF THE PREFERRED EMBODIMENTS

The reaction between an olefin with a compound containing a carboxylate moiety having at least one carbon atom on the alpha carbon atom in the presence of an ion of manganese, cerium, or vanadium in a valency state higher than the lowest valency state to produce a butyrolactone is exemplified in the following equation form using ethylene as the olefin, acetic acid as the compound containing the carboxylate moiety having at least one carbon atom on the alpha carbon atom, and manganese in its trivalent state:

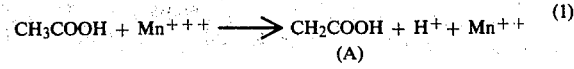

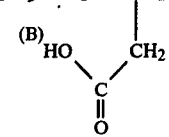

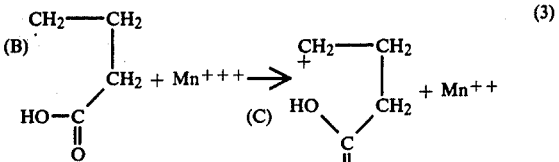

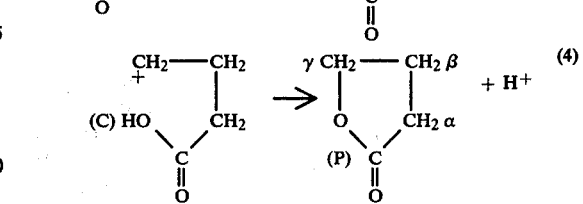

In equation (4), the alpha ($\alpha$), beta ($\beta$), and gamma ($\gamma$) carbon atoms of the gamma-butyrolactone product are labeled. The overall reaction is:

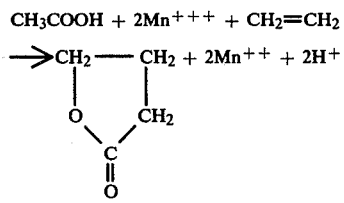

showing that one mole of ethylene in the presence of the manganic ion ($Mn^{+++}$) gives one mole of lactone.

As shown in equation (1), the acetic acid reacts with the manganic ion, $Mn^{+++}$, to form the carboxymethyl free radical, (A), a hydrogen ion, $H^+$, and manganous ion, $Mn^{++}$. According to the reaction of equation (2), which takes place in the presence of the ethylene reactant and the products of equation (1), the carboxymethyl free radical, (A), adds to the double bond of the ethylene forming the free radical, (B). The free radical, (B), then reacts with manganic ion to form the cation, (C), and manganeous ion, as shown in equation (3). As shown in equation (4), the cation, (C), cyclizes to form the gamma-butyrolactone product, (P), and a hydrogen ion, $H^+$.

From the foregoing, it will be appreciated that the substituents on the alpha carbon atom of the gamma-butyrolactone product are the substituents on the alpha carbon atom of the carboxylic acid, the alpha carbon atom on the carboxylic acid being the carbon atom adjacent to the carboxy group,

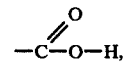

and the substituents on the beta and gamma cabon atoms of the gamma-butyrolactone product are the substituents on the carbon atoms joined by the double bond of the olefin.

Various olefins may be employed in the preparation of the gamma-butyrolactones by the process of the invention. These olefins may be monoolefins or diolefins and may be acyclic monoolefins or diolefins and cyclic monoolefins or diolefins. The diolefins may be conjugated or non-conjugated. The acyclic monoolefins may be straight chain or branched chain monoolefins and may contain between 2 to 200 carbon atoms. Preferably, however, the acrylic monoolefins contain between 2 and 92 carbon atoms and, still more preferably, contain between 2 and 10 carbon atoms. The acyclic diolefins may contain between 3 and 8 carbon atoms. The cyclic monoolefins may contain between 5 and 8 carbon atoms and the cyclic diolefins may also contain between 5 and 8 carbon atoms. The acyclic monoolefins may contain one or more aromatic groups, preferably phenyl groups. Further, the acyclic monoolefins may contain chlorine or bromine substituents or a carboxy or carboxymethyl substituent.

Suitable illustrative olefins include ethylene, propylene, the butenes, pentenes, hexenes, heptenes, octenes, nonenes, and decenes. Other acyclic monoolefins which may be employed are olefin oligomers such as propylene and isobutylene tetramer, isobutylene trimer, and propylene pentamer and hexamer. Other suitable illustrative olefins include allene, butadiene, pentadiene, isoprene, biallyl, heptadiene, and bimethallyl. Still other suitable illustrative olefins include cyclopentene, cyclohexene, cycloheptene, cyclooctene, cyclopentadiene, cyclohexadiene, cycloheptadiene, and cyclooctadiene. Acyclic monoolefins containing one or more aromatic groups include styrene, methyl styrene, stilbene, 1,1-diphenyl ethylene, and methyl cinnamate. Representative olefins containing chlorine, bromine, carboxy or carboxymethyl substituents include bromostyrene, methyl cinnamate, methylacrylate, dimethyl maleate, polychloroethylene, oleic acid and methyl oleate.

It will be seen that the foregoing olefins are those of the formula

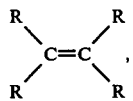

wherein one or more of the Rs are hydrogen, straight or branched chain alkyl groups, the total number of carbon atoms in the alkyl groups being between 1 and 198, an alkenyl group containing 1 to 6 carbon atoms, a phenyl group, a phenyl group or an alkyl group of no more than 7 carbon atoms each containing a chlorine, bromine, carboxy or carboxymethyl substituent, and, where one R is other than hydrogen, it may be joined to each of the carbon atoms of the double bond.

The carboxylic acid employed in the preparation of the gamma-butyrolactones by the process of the invention must, as indicated in the foregoing equations (1) to (4), contain at least one hydrogen substituent on the alpha carbon atom. The other substituents include hydrogen, saturated or unsaturated alkyl groups containing 1 to 10 carbon atoms, cyano, and alkyl carboxy or alkyl carboxymethyl groups. The alkyl carboxy or alkyl carboxymethyl groups may contain 1 to 6 carbon atoms in the alkyl portion thereof.

Suitable illustrative carboxylic acids include acetic, propanoic, the butanoic, the pentanoic, the hexanoic, the heptanoic, the octanoic, the nonanoic, the decanoic, the undecanoic, and the dodecanoic acids. Other suitable illustrative carboxylic acids include the butenoic, pentenoic, hexenoic, heptenoic and dodecanoic acids. Still other suitable illustrative carboxylic acids include cyanoacetic, succinic, glutaric, adipic, pimelic, suberic, and azelaic acids and their mono-methyl esters.

It will be seen that the foregoing acids are those of the formula

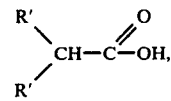

wherein one or both of the R's are hydrogen, a straight or branched chain alkyl or alkenyl group containing 1 to 10 carbon atoms, a cyano, or an alkyl carboxy

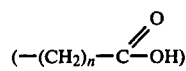

or alkyl carboxymethyl

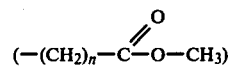

group where the alkyl group contains 1 to 6 carbon atoms, i.e., n=1-6.

As will be apparent, some of the olefins named above can contain carboxy groups having at least one hydrogen atom on the alpha carbon atom and some of the acids named above may contain an olefinic group. These olefins and acids therefore can act either as an olefin or acid. If an olefinic acid is reacted with an olefin, the olefinic acid will react as an acid and if reacted with an acid, the olefinic acid will react as an olefin. If two olefinic acids are reacted, a portion of the amount of each in the reaction mixture will act as an olefin and the remainder as an acid.

The reaction for the production of the gammabutyrolactones is carried out, as stated, in the presence of an ion of manganese, cerium, or vanadium. The ion of manganese, cerium, or vanadium must be in a valency state higher than its lowest valency state. Manganese can exist in five valency states, namely, in valency states of 2, 3, 4, 6, and 7. Cerium can exist in two valency states, namely, in valency states of 3 and 4. Vanadium can exist in three valency states, namely, in valency states of 2, 3, and 5. Thus, in carrying out the reaction, the ion of manganese must be in a valency state of 3, 4, 6, or 7, the ion of cerium must be in a valency state of 4, and the ion of vanadium must be in a valency state of 3 or 5.

The preferred ion for the gamma-butyrolactone producing reaction is trivalent manganese, i.e., manganese ion in a valency state of 3 or $Mn^{+3}$. As indicated in the foregoing equations (1) to (5), the trivalent manganese ion is reduced during the reaction to bivalent manganese, i.e., manganese in a valency state of 2 or $Mn^{+2}$. The trivalent manganese, or manganic ion, may be provided in the gamma-butyrolactone producing reaction mixture by including therein manganic acetate dihydrate. This compound may be formed by refluxing an acetic acid solution of manganous acetate, i.e., acetate where the valency state of the manganese is 2, or $Mn^{+2}$, with potassium permanganate. Other suitable manganic ion-producing compounds or mixtures for producing manganic ion include (1) anhydrous manganic acetate, (2) a mixture of activated (i.e, freshly prepared or acid treated) manganese dioxide and acetic acid, (3) a mixture of manganese sesquioxide and acetic acid, and (4) a mixture of manganic manganous oxide ($Mn_3O_4$) and acetic acid. The manganic ion may also be provided by including in the reaction manganic chloride, manganic fluoride, manganic hypophosphate dihydrate, manganic sulfate, manganic phosphate monohydrate, or manganic pyrophosphate.

The manganese ion in higher valent form may also be provided by manganese ion in a valency state higher than 3. For example, the manganese ion may be in a valency state of 4, 6, or 7. Manganese in a valency state of 4 may be obtained from a mixture of manganese dioxide ($MnO_2$) and acetic acid. The manganese ion in a valency state of 6 may be provided by the manganate of sodium, potassium, ammonium, lithium, magnesium, strontium, calcium, or barium. The manganese ion in a valency state of 7 may be provided by the permanganate of sodium, potassium, ammonium, or magnesium.

In addition to the foregoing, the manganese ion in a higher valency state may be provided by mixtures of manganese ions. Such mixtures include those of manganous ion, $Mn^{+2}$, plus any manganese ions having a valency state of 3, 4, 6, or 7. The manganic manganous oxide mentioned above is a mixture of manganese ions in the valency states of 2 and 3.

The compound chosen to provide the manganese ion in the higher valency state should have solubility, preferably complete solubility in the gamma-butyrolactone producing reaction mixture.

The cerium ion of higher valency state may be provided in the reaction mixture for producing the gammabutyrolactone by including therein ceric acetate. This compound may be formed by reacting a ceric salt soluble in acetic acid with acetic acid. Such salts include ceric ammonium nitrate, ceric nitrate, and ceric sulfate. Alternatively, the cerium ion of higher valency state may be provided in the reaction mixture for producing the gamma-butyrolactone by including therein a ceric salt, other than the acetate, soluble in the reaction mixture. Such ceric salts soluble in the reaction mixture include those mentioned above.

The vanadium ion of higher valency state may be provided in the reaction mixture for producing the gammabutyrolactone by including therein vanadic ($V^{+2}$ or $V^{+5}$) acetate. This compound may be formed by reacting a vanadic salt soluble in acetic acid with acetic acid. Such salts include vanadium trichloride, vanadium tribromide, vanadium trifluoride trihydrate, vanadium tetrafluoride and ammonium metavanadate. Alternatively, the vanadium ion of higher valency state may be provided in the reaction mixture for producing the gammabutyrolactone by including therein a vanadic salt, other than the acetate, soluble in the reaction mixture. Such vanadic salts soluble in the reaction mixture include those mentioned above.

The compound providing the ion of manganese, cerium, or vanadium in a valency state higher than its lowest valency state may be added per se to the reaction mixture or, if desired, it may be formed in situ. In situ formation may suitably be accomplished by adding to the reaction mixture, for example, a manganous compound like manganous acetate together with a solvent therefor like acetic acid and also adding an oxidizing agent so that the manganous ion is oxidized to at least manganic ion, $Mn^{+++}$. Suitable oxidizing agents include nitric acid, chlorine, oxygen, air, ozone, various peroxides like peracetic acid and hydrogen peroxide, or intermediate peroxides or hydroperoxides, such as tertiary butyl hydroperoxide, resulting from the air oxidation of hydrocarbons. Electrochemical oxidation is a suitable oxidizing procedure. Where an oxidizing agent is added to the reaction mixture, the oxidizing agent can oxidize the olefin and, in this case, the ion of manganese, cerium, or vanadium in its lower valency state is maintained in high concentration in the reaction mixture in order to effect oxidation of the ion preferentially so that of the olefin.

The reaction mixture for the production of the gamma-butyrolactones may also contain a solvent. The use of a solvent is indicated where any of the reactants are not otherwise soluble in the reaction mixture under the reaction conditions. Any solvent inert with respect to the reactants under the reaction conditions and which will remain in the liquid state under the reaction conditions may be employed. A suitable solvent is a saturated hydrocarbon such as hexane and higher alkanes having up to 30 carbon atoms. Ethers may also be employed as a solvent.

A carboxylic acid may also be employed as a solvent. However, where a carboxylic acid other than the carboxylic acid desired for reaction with the olefin to produce the gamma-butyrolactone is employed as a solvent, the solvent carboxylic acid will compete with the reactant carboxylic acid to produce gamma-butyrolactone. The extent to which the solvent carboxylic acid will compete with the reactant carboxylic acid will depend upon the relative reactivities of the two acids and the relative proportions of each in the reaction mixture. Thus, where the reactivities of the two acids, as measured by their disassociation constants, are substantially similar, the extent of competition will depend primarily upon the relative proportions, from a molar standpoint, of the two acids in the reaction mixture. The reaction product in this instance will be a mixture of gamma-butyrolactone derived from the reactant carboxylic acid and gamma-butyrolactone derived from the solvent carboxylic acid, the relative proportions of the gamma-butyrolactones depending upon the relative proportions of the acids in the reaction mixture. On the other hand, where the reactivities of the two acids are substantially dissimilar, the more reactive acid will compete with the less reactive acid to the practical exclusion of the less reactive acid regardless of the relative proportions of each in the reaction mixture. However, where the acids have equivalent reactivities, such as acetic and propionic acids, it is convenient to add the ion to the reaction mixture as the salt of the acetic acid while using the propionic acid as the solvent and the lactone product will be that of the propionic acid.

Carboxylic acids which may be employed as solvents may be straight or branched chain. Included among these acids are acetic acid, propionic acid and the butanoic and pentanoic acids. Acid anhydrides may also be used as solvents. Water or paraffinic hydrocarbons may be used in conjunction with carboxylic acid solvents. Dimethyl acetamide may be employed as a solvent.

Considering now the conduct of the reaction, the ratio of the olefin in the reaction mixture may be from 0.01 to 3 moles, preferably 0.25 to 1 mole per mole of ion of manganese, cerium, or vanadium. The carboxylic acid is preferably in an amount to provide at least one mole per mole of olefin. The solvent, if employed, will be present in an amount sufficient to dissolve a portion of the reactants. The reaction is carried out by subjecting the reactants to a temperature between 20° C. and 250° C., preferably between 50° C. and 180° C. The rate of reaction will, of course, depend upon the temperature employed and will also depend upon the activity of the carboxylic acid. With the more reactive carboxylic acids, such as cyanoacetic acid, lower temperatures may be employed with satisfactorily rapid rates of reaction. Refluxing may be employed. The reaction may be carried out under pressure, if necessary, to maintain a liquid phase. The reaction time may extend from one hour to 10 hours. An inert atmosphere, such as one of nitrogen, carbon dioxide, helium, or the like, is desirably maintained over the reaction mixture to lessen or avoid oxidation by air. Where the olefin employed readily polymerizes, it is preferred to add it slowly to the remainder of the reaction mixture to minimize polymerization.

At the conclusion of the reaction, separation of the lactone product may be effected by conventional distillation, fractional crystallization, extraction, and the like with or without the aid of conventional filtration or centrifugation. For example, in a reaction mixture containing lactone product from acetic acid and ethylene, manganous acetate, and any unreacted ethylene, the mixture may be filtered to remove any solids and then subjected to distillation, using vacuum if necessary. The lactone has a higher boiling point than the acetic acid and the acetic acid, and any of the normally gaseous ethylene that may be remaining in the reaction mixture, will distill off leaving the lactone product.

High yields of lactone are obtainable by the process of the invention. Up to 95%, or more, of the olefin may be converted to lactone indicating that the carboxylic acid has selectivity to addition to the double bond of the olefin in the presence of the ion of manganese, cerium, or vanadium. Without restricting the invention to the theoretical considerations, it is believed that, owing to the use of the ion of manganese, cerium, or vanadium, the selectivity is a result of the relatively fast oxidation of the free radical (B) (note the foregoing equation (3)) to the cation (C). Where manganic ion is employed, about 1 mole of lactone may be formed per 2 moles of manganic ion reduced and, as shown in the examples following, lactone yields of about 50% to about 85% based on the manganic ion reduced are obtainable. On the basis of olefin consumed, the yields are higher. The addition of a potassium salt, or other alkali metal salt of the carboxylic acid, may help to suppress formation of minor side products. It also increases the boiling point of the reaction mixture and thereby permits the use of higher temperatures to facilitate reaction without the use of pressure.

The lactone product ddepends on the starting olefin and on the carboxylic acid. Thus, with ethylene as the starting olefin, and using acetic acid and manganous acetate dissolved in acetic acid, the product is a simple lactone like gamma-butyrolactone,

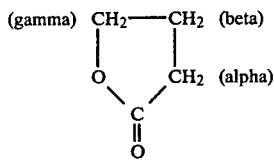

where the alpha, beta, and gamma carbons are substituted only by hydrogen. As the starting olefin becomes more complex, so too the lactone product becomes complex, as indicated in Examples 1-8, where lactones with beta and/or gamma substituents are shown. These products may be named on the basis of the formula just given; thus the product of Example 1 is beta-methyl-gamma-phenyl-butyrolactone; that of Example 2 is gamma, gamma-methyl-phenyl-butyrolactone, etc. With propionic acid and manganic acetate dissolved in propionic acid, and using ethylene as the starting olefin, the resulting lactone is alpha-methyl-butyrolactone,

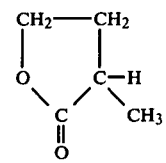

and as is apparent, has a methyl substituent in the alpha position. An indication of additional products is given below.

The manganous compound that is formed as a consequence of the reduction of the manganic compound may, as already indicated, be saved and used to regenerate the manganic compound. Thus, where the manganous compound is manganous acetate, it is desirably isolated from the reaction mixture, heated at 200°–300° C. to form MnO, acetone, and carbon dioxide, and the oxide then heated in air or oxygen to form $MnO_2$, $Mn_2O_3$, and/or $Mn_3O_4$. On dissolving these oxides in acetic acid, there is formed manganic acetate, and this solution is of use to prepare a lactone in accordance with equations (2) and (3) above. The acetone, of course, is valuable enough to recover.

Alternatively, the isolated manganous acetate may be dissolved in acetic acid and the solution electrolyzed, using a carbon or other suitable anode, to form manganic acetate, the resulting electrolyzed solution being directly usable in a lactone-forming reaction. Where the manganous acetate is already in solution in acetic acid, no preliminary isolation step is necessary as such solution may be charged to the electrolysis cell and electrolyzed.

Or the isolated manganous acetate may be dissolved in water, the solution buffered to pH 6 to 8 by means of ammonium chloride or other suitable buffer, and air or oxygen passed through the solution to produce manganese sesquioxide. This oxide is filtered and dissolved in acetic acid to form a solution of manganic acetate.

The isolated manganous acetate may also be treated with an oxidizing agent like concentrated or fuming nitric acid plus acetic anhydride to produce anhydrous manganous acetate, which is useful per se in the lactone-forming reaction.

As a further alternative, the manganous acetate, either isolated or in acetic acid solution, may be mixed with acetic acid and with activated $MnO_2$ to form manganic acetate. To obtain activated $MnO_2$, one can freshly prepare this oxide, or can treat an existing sample with a dilute mineral acid following this with water washing and drying.

Manganous acetate can also be oxidized to manganic acetate by treatment with potassium permanganate.

The foregoing regeneration procedures generally apply to other manganous compounds besides the acetate; and with suitable modifications they are applicable to the regeneration of the other higher-valent compounds of cerium and vanadium from lower-valent forms thereof. It will be appreciated that the regeneration step permits the manganese, cerium, or vanadium compound to be used over and over and therefore represents a significant economy.

Whereas the invention has been described herein specifically in connection with a carboxylic acid having at least one hydrocarbon atom on the alpha carbon atom as the compound containing a carboxylate moiety having at least one hydrogen atom on the alpha carbon atom, it is to be understood that other compounds may also provide the necessary carboxylate moiety. Thus, the necessary carboxylate moiety may be provided by a manganese, cerium, or vanadium carboxylate having at least one hydrogen atom on the alpha carbon atom, the metal being in a valency state higher than its lowest valency state, where a solvent other than a carboxylic acid having at least one carbon atom on the alpha carbon atom, such as dimethyl acetamide is employed. In this instance, taking manganic acetate as an example, the reaction proceeds as follows:

$$Mn(OCOCH_3)_3 \rightarrow CH_2COOH + Mn(OCOCH_3)_2 \qquad (5)$$

to produce the free radical (A) as in the foregoing equation (1). The reaction proceeds subsequently as indicated in the foregoing equations (2)–(4), the $Mn^{+++}$ ion in equation (3) being provided by the manganic acetate. The necessary carboxylate moiety may also be provided by the anhydride of a carboxylic acid having at least one hydrogen atom on the alpha carbon atom. Thus, taking acetic anhydride and taking $Mn_2O_3$ as the compound providing the ion of manganese, cerium, or vanadium in a valency state higher than its lowest valency state, the reaction proceeds as follows:

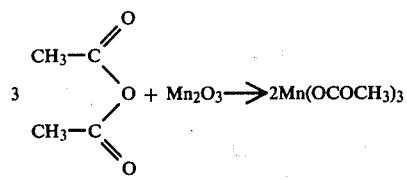
(6)

and the manganic acetate produces the free radical (A) as in the foregoing equation (5), the reaction proceeding subsequently as indicated in the foregoing equations (2)–(4), the $Mn^{+++}$ ion in equation (3) being provided by the manganic acetate. The necessary carboxylate moiety may also be provided by a salt of manganese, cerium, or vanadium other than a carboxylate, the manganese, cerium, or vanadium being in a valency state higher than its lowest valency state, in the presence of a carboxylate other than that of manganese, cerium, or vanadium, the carboxylate having at least one hydrogen atom on the alpha carbon atom. Thus, taking manganic chloride as the salt of manganese, cerium, or vanadium and potassium acetate as the carboxylate, the reaction proceeds as follows:

$$MnCl_3 + 3CH_3COOK \rightarrow Mn(OCOCH_3)_3 + 3KCl \qquad (7),$$

the manganic acetate producing the free radical (A) as in equation (5) and the reaction proceeding subsequently as indicated in the foregoing equations (2)–(4), the $Mn^{+++}$ ion in equation (3) being provided by the manganic acetate.

The following examples illustrate the preparation of lactones from several olefins at different reaction conditions and by use of various sources of reducible metal ions.

EXAMPLES 1–8

In separate procedures, each of the olefins listed in the table below was dissolved in glacial acetic acid to form a solution ranging from 0.05 to 1 molar with respect to the olefin. To such solution there were added 2 mole equivalents of manganic acetate, $Mn(C_2H_3O_2)_3.2H_2O$ and about 300 grams per liter of anhydrous potassium acetate, the latter being employed to suppress any undesired side products. The resulting solution was then heated to refluxing under a nitrogen atmosphere until the brown manganic color disappeared, this step requiring from 0.5 to 6 hours, depending on the olefin. Thereafter the reaction mixture was analyzed for lactone content by means of vapor phase chromatography. The following table shows the lactone formed from each starting olefin, together with the yield, the latter being calculated on the basis of $Mn^{+3}$ consumed. No attempt was made to optimize the yield, although it may be noted that the yields are higher when based on the consumed olefin.

TABLE I

| EX. NO. | OLEFIN | LACTONE | YIELD % |
|---|---|---|---|
| 1 | trans-beta-methylstyrene | 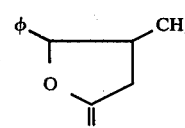 (a) | 79 |
| 2 | a-methylstyrene | 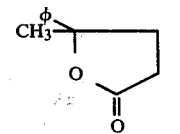 | 74 |
| 3 | octene-1 | 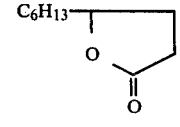 | 74 |

TABLE I-continued

| EX. NO. | OLEFIN | LACTONE | YIELD % |
|---|---|---|---|
| 4 | trans-octene-4 | 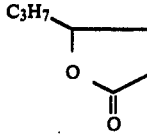 C$_3$H$_7$, C$_3$H$_7$ (b) | 56 |
| 5 | cyclooctene | 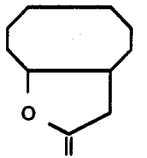 | 65 |
| 6 | trans-stilbene | 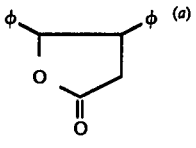 φ, φ (a) | — |
| 7 | styrene | 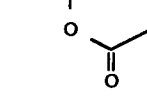 C$_6$H$_5$ | — |
| 8 | cis-beta-methylstyrene | 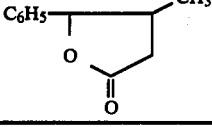 C$_6$H$_5$, CH$_3$ | 79 |

(a) Only one isomer was obtained (presumably the trans).
(b) Two isomers in the ratio of 5:1 were obtained.

EXAMPLES 9-17

In each of these examples, the operations described in Examples 1-8 were repeated employing the olefins listed in Table II below. The table also lists the lactones obtained. In each case, the yield of the lactone was between 50-75% based on the Mn$^{+3}$ consumed.

TABLE II

| EXAMPLE NO. | OLEFIN | LACTONE |
|---|---|---|
| 9 | 1,1-diphenyl-ethylene | gamma-diphenyl butyrolactone |
| 10 | cis-octene-4 | beta-n-propyl-gamma-n-propyl butyrolactone |
| 11 | 2-methylheptene-1 | gamma-methyl-gamma-n-pentyl butyrolactone |
| 12 | p-methylstyrene | gamma-p-methylphenyl butyrolactone |
| 13 | p-bromostyrene | gamma-p-bromophenyl butyrolactone |
| 14 | m-bromostyrene | gamma-m-bromophenyl butyrolactone |
| 15 | decene-1 | gamma-n-octyl butyrolactone |
| 16 | dodecene-1 | gamma-n-decyl butyrolactone |
| 17 | hexadecene-1 | gamma-n-tetradecyl butyrolactone |

EXAMPLES 18-25

In each of the following examples, the olefin, listed in Table III, was employed. In each example, to a 1.3 liter pyrex bomb were added 29.24 grams (0.1 mole) of manganic acetate dihydrate and 950 milliliters of a 10% solution of potassium acetate in acetic acid. The mixture was degassed by bubbling nitrogen through it for a period of 20 minutes. The manganic acetate dihydrate dissolved upon warming the mixture to 50° C. Then, in rapid succession 34.03 grams (0.4 mole) of cyano-acetic acid and 0.200 mole of the olefin were added. These were rinsed into the bomb with 50 milliliters of acetic acid. After one hour at 50° C., the acetic acid was distilled from the mixture using a rotovap. The residue was taken up in 1500 milliliters of water and extracted with 400, 300, and 200 milliliter-portions of diethyl ether. The combined ether layers were then extracted with sufficient cold 10% aqueous solution of sodium carbonate to form a slightly basic aqueous layer. The basic layer was then extracted once with diethyl ether. The combined ether layers were dried over anhydrous magnesium sulfate, filtered, and evaporated to a constant weight. Table III lists the lactone obtained, and the yield, for each of the olefins.

TABLE III

| EXAMPLE NO. | OLEFIN | LACTONE | YIELD % |
|---|---|---|---|
| 18 | octene-1 | alpha-cyano-gamma-n-hexyl butyrolactone | 60 |
| 19 | styrene | alpha-cyano-gamma-phenyl butyrolactone | 41 |
| 20 | alpha-methylstyrene | alpha-cyano-gamma-methyl-gamma-phenyl | 43 |

TABLE III-continued

| EXAMPLE NO. | OLEFIN | LACTONE | YIELD % |
|---|---|---|---|
| 21 | cis-beta-methylstyrene | butyrolactone alpha-cyano-beta-methyl-gamma-phenyl butyrolactone | 50 |
| 22 | trans-beta-methylstyrene | alpha-cyano-beta-methyl-gamma-phenyl butyrolactone | 50 |
| 23 | octene-4 | alpha-cyano-beta, gamma-di-n-propyl butyrolactone | 49 |
| 24 | isoprene | 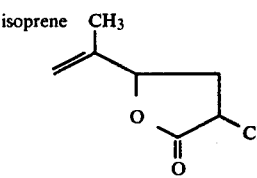 minor product    and    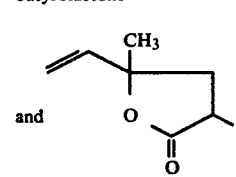 major isomer (a) | 44 |
| 25 | 2,5-dimethylhexadiene-1,5 | 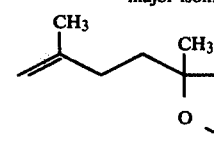 | 20 |

(a) The ratio of the major isomer to the minor product was 8:1.

EXAMPLES 26–37

In each of these examples, a different olefin was employed. About 0.015 mole of the olefin and 8.1 gram (0.03 mole) of manganic acetate dihydrate were added to 73 milliliters of glacial acetic acid containing 10% of potassium acetate. The mixture was then sealed in a glass tube and heated in an oil bath at temperatures between 140° C. and 180° C. When the characteristic brown color due to manganic ion had disappeared, the reaction was stopped and the reaction mixture extracted with diethyl ether and water. Table IV lists the olefin, the lactone obtained, and the yield.

TABLE IV

| EXAMPLE NO. | OLEFIN | LACTONE | YIELD % |
|---|---|---|---|
| 26 | isobutylene | gamma-dimethyl butyrolactone | 30 |
| 27 | 3-methylbutene-1 | gamma-iso-propyl butyrolactone | 50 |
| 28 | methylcinnamate | 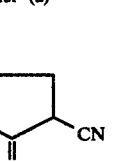 | 45 |
| 29 | methylacrylate | 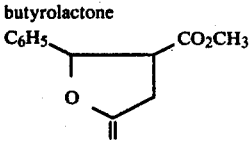 | — |
| 30 | dimethylmaleate | 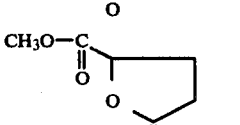 | — |
| 31 | hexadiene-1,5 | 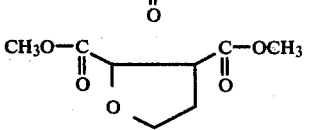 | 25 |

TABLE IV-continued

| EXAMPLE NO. | OLEFIN | LACTONE | YIELD % |
|---|---|---|---|
| 32 | octadiene-1,7 | | 26 |
| 33 | 2,5-dimethylhexadiene-1,5 | | — |
| 34 | butadiene | gamma-vinyl butyrolactone | 30 |
| 35 | isoprene | (3 parts) and (1 part) | 50 |
| 36 | cyclopentadiene | | — |
| 37 | cyclohexadiene-1,3 | | — |

EXAMPLE 38

Styrene in an amount of 2.1 grams and 11.65 grams of manganic acetate, $Mn(C_2H_3O_2)_3.2H_2O$, comprising two equivalents of $Mn^{+3}$ based on titration value, were refluxed under nitrogen in 200 milliliters of propionic acid containing 20 grams of potassium propionate. In less than an hour, a 50% yield of alpha-methyl-gamma-phenyl butyrolactone was obtained.

EXAMPLE 39

The procedure of Example 38 was repeated except that isobutyric acid was used in place of propionic acid and sodium isobutyrate was used in place of potassium propionate. The lactone obtained was alpha-dimethyl-gamma-phenyl butyrolactone.

EXAMPLE 40

To a mixture of 700 grams of succinic acid and 300 milliliters of acetic acid at reflux were added 14.1 grams of monosodium succinate, 40 grams of potassium acetate, and 12 grams of octene-1. Manganic acetate dihydrate in the amount of 27 grams (0.1 mole) was added over a period of 15 minutes. When the brown color had disappeared, three more grams of octene-1 and 27 more grams of manganic acetate dihydrate were added. When the reaction was completed, the mixture was diluted with water and extracted with ether. The reaction product obtained in 25% yield was crystallized from petroleum ether and melted at 76°–76.5° C. This was identified as the lactone shown below by analytical and spectral means:

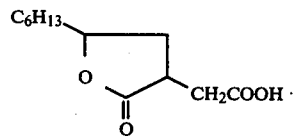

EXAMPLE 41

Manganese acetate tetrahydrate $(Mn(OAc)_2.4H_2O)$ in the amount of 860 grams (3.5 moles) was added to 6 liters of acetic acid. The mixture was heated to 116° C. with nitrogen purge. Potassium permanganate in the amount of 132 grams (0.84 mole) was added slowly over ½ hour. The typical brown color of $Mn^{+3}$ ion appeared immediately upon addition. The solution was stirred at about 100° C. for ½ hour, and potassium acetate in the amount of 1800 grams was then added in 600-gram increments. The reaction temperature was increased by taking solvent off in a Dean Stark side arm. After 1 liter of solvent was taken off, 200 milliliters of decene-1 were added to the reaction mixture. The mixture was then kept at reflux until the brown $Mn^{+3}$ color disappeared. The reaction mixture was then cooled down and 1 liter of ice water was added. The resulting mixture was extracted 4 times with 1 liter increments of benzene. The benzene was stripped, leaving a residue of 224 grams of product which analyzed for 88% pure gamma-n-octyl butyrolactone. The yield was 47.5% based upon the $Mn^{+3}$ ion.

EXAMPLE 42

Octene-1 in an amount of 2.2 grams and 23.6 grams of ceric acetate were refluxed under nitrogen in 200 milliliters of glacial acetic acid containing 60 grams of potassium acetate for less than 0.4 hour, there being obtained a 31% yield of gamma-n-hexyl butyrolactone.

EXAMPLE 43

Styrene in the amount of 20 grams was dissolved in 100 milliliters of acetic acid containing 10% potassium acetate. Ceric acetate in the amount of 0.005 mole was added and the reaction mixture was heated in a sealed tube at 110° C. overnight. The lactone, gamma-phenyl butyrolactone, was obtained in 70% yield.

EXAMPLE 44

The procedure of Example 43 was repeated, except that propionic acid and sodium propionate were used in place of acetic acid and potassium acetate. Alpha-methyl-gamma-phenyl butyrolactone was obtained in 60% yield.

EXAMPLE 45

The procedure of Example 43 was repeated except that isobutyric acid and sodium isobutyrate were employed in place of acetic acid and potassium acetate. The lactone obtained was alpha-dimethyl-gamma-phenyl butyrolactone.

EXAMPLE 46

Ammonium meta-vanadate in the amount of 0.01 mole (1.17 grams) was added to 100 milliliters of acetic acid containing 0.02 mole (2.24 grams) of octene-1 in an ampoule. This solution was purged with nitrogen. The ampoule was sealed and placed in a 145° C. bath. The color of the solution went from deep yellow to dark blue. After 2.5 hours, the sample was cooled and worked up by diluting with ether and washing the ether with ice water and cold aqueous saturated sodium bicarbonate. The ether extract was dried with sodium sulfate and stripped on a rotovap. This gave a major product identified as

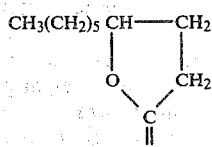

EXAMPLE 47

Ammonium meta-vanadate in the amount of 0.01 mole (1.17 grams) was added to 100 milliliters of 10% potassium acetate in acetic acid. The reaction mixture was heated to reflux with nitrogen purge. Octene-1 in the amount of 0.02 mole (2.24 grams) was added, followed by 0.04 mole (3.4 grams) of cyano acetic acid. The solution immediately turned from yellow to dark blue. The solution was refluxed for 15 minutes, cooled, and worked up by diluting with ether and washing the ether with ice water and cold saturated aqueous sodium bicarbonate. The ether extract was dried with sodium sulfate and the solvent stripped off on a rotovap. The major product obtained was identified as

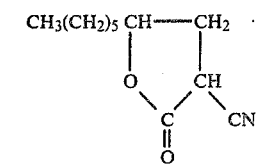

EXAMPLE 48

About 1.69 g. (0.015 mole) octene-1 and 8.1 g. (0.03 mole) manganic acetate were added to 73 ml. glacial acetic acid and the mixture sealed in a tube. No potassium acetate was used. The tube was placed in an oil bath maintained at 138° C., and after 4 hours the characteristic dark brown color due to manganic ion disappeared. The reaction was stopped and the reaction mixture worked up by extracting with ether and water. Gamma-n-hexyl-butyrolactone was obtained in a yield of 2.0 g., comprising 78% of theory.

EXAMPLE 49

About 1.69 g. octene-1 and 7.0 g. anhydrous manganic acetate were added to 150 ml. glacial acetic acid containing 45 g. potassium acetate and the mixture refluxed under nitrogen. The reaction was complete in less than two hours, and gamma-n-hexyl-butyrolactone was recovered in 65% yield.

EXAMPLE 50

Octene-1 in an amount of 3.37 g. and 4.8 g. of freshly prepared $MnO_2.4H_2O$ were mixed with and heated under nitrogen in 300 ml. glacial acetic acid containing 90 g. potassium acetate. After a reaction time of less than two hours, gamma-n-hexyl-butyrolactone was obtained in 74% yield.

EXAMPLE 51

Octene-1 in an amount of 2.24 g. and 5.1 g. of $Mn_2O_3$ (comprising two equivalents of $Mn^{+3}$ based on titration value) were refluxed under nitrogen in 200 ml. glacial acetic acid containing 60 g. potassium acetate. After a period of less than two hours, gamma-n-hexyl-butyrolactone was obtained in a yield of 61%.

EXAMPLE 52

Octene-1 in an amount of 2.2 g. and 23.6 g. of ceric ammonium nitrate, $Ce(NH_4)_2(NO_3)_6$, were refluxed under nitrogen in 200 ml. glacial acetic acid containing 60 g. potassium acetate for less than 0.5 hour, there being obtained a 48% yield of gamma-n-hexyl-butyrolactone.

EXAMPLE 53

Octene-1 in an amount of 2.24 g. and 11.65 g. of manganic acetate, $Mn(C_2H_3O_2)_3.2H_2O$, (comprising two equivalents of $Mn^{+3}$ based on titration value), were refluxed under nitrogen in 200 ml. propionic acid containing 20 g. potassium propionate. In less than an hour a good yield of alphamethyl-gamma-n-hexyl-butyrolactone was obtained.

EXAMPLE 54

The work of Example 52 was repeated, except that styrene was used in place of octene-1. The product was gamma-phenyl-butyrolactone.

EXAMPLE 55

The work of Example 53 was repeated, with the same results, except that 3.2 g. of freshly prepared $MnO_2$ were used in place of the manganic acetate.

EXAMPLE 56

Potassium permanganate in the amount of 15.8 grams was added at 40° C. to 92 grams of manganous acetate, $Mn(OCOCH_3)_2$, in acetic acid. To the resulting solution were added 94 grams of polybutene-1 having a molecular weight of 800, i.e., containing 64 carbon atoms, and the mixture was refluxed under nitrogen for 4 hours. The lactone product was extracted from the reaction mixture with hexane and was obtained in 55% yield based on infra-red and acid determination value.

EXAMPLE 57

A stock solution was prepared by heating at 115° C. 500 milliliters of acetic acid, 150 grams of potassium acetate, and 245 grams of manganous acetate tetrahydrate, $Mn(OCOCH_3)_2.4H_2O$. A 50-milliliter aliquot of the stock solution was added to 2 milliliters of a 0.312 molar solution of tertiary butyl hydroperoxide in acetic acid. The solution also contained 400 microliters of octene-1. After heating, a hexyl gamma-butyrolactone was obtained with a 65% yield based on the tertiary butyl hydroperoxide.

EXAMPLE 58

Acetic acid was reacted in the presence of ceric acetate with 4-decyne-1-ene to form gamma-2-octyne butyrolactone. The selectivity of the addition of the carboxymethyl radical to the terminal olefin relative to its addition to the internal acetylenic bond was in excess of 5 to 1.

The gamma-2-octyne butyrolactone was hydrogenated at atmospheric pressure over palladium deposited on carbon to produce gamma-2-octene butyrolactone. The latter product, synthesized as described, is a mammalian pheromone identified and determined by others from studies of the male tarsal scent in black-tailed deer.

Gamma-butyrolactones are well known compounds and have various known uses. Thus, the gamma-butyrolactone produced by the process of the invention from acetic or propionic acid and cyclohexene may be employed as agents against animal parasites, for example, as anthelmintics; and as agents for destroying noxious pests (U.S. Pat. No. 2,007,813). The gamma-butyrolactone produced by the process of the invention from cyanoacetic acid and ethylene may be employed as an insecticide or larvacide providing protection to articles commonly infested such as agricultural products, weaving apparel and the like (U.S. Pat. No. 2,362,614). The gamma-butyrolactones produced by the process of the invention from propionic acid and isobutene, acetic acid and $(HOOC-CH_2-CH_2)C(CH_3)=CH_2$, and $HOOC-(CH_2-)_3-CH(CH_3)-COOH$, and isobutene can be used in perfumery and for masking odors in many kinds of compositions; as chemical intermediates, reacting with alcohols to form esters, with ammonia, amines and other bases, halogen acids, etc.; and as softeners and plasticizers for polymeric material such as polyvinyl chloride (U.S. Pat. No. 2,839,538). The gamma-butyrolactone produced by the process of the invention from glycollic acid and ethylene exhibits activity as an inhibitor of gastric secretion (U.S. Pat. No. 2,995,576).

The gamma-butyrolactones produced by the process of the invention from acetic, propionic and butyric acids and isobutene and 3-ethyl, butene-1 are valuable solvents and useful intermediates for the preparation of pyrrolidones, chloro acids, thio acids and other organic compounds (U.S. Pat. No. 3,004,989). The gamma-butyrolactone produced by the process of the invention from acetic acid and ethylene may be used as a solvent for softening cellophane, parchment, and the like (U.S. Pat. No. 3,166,574). The gamma-butyrolactone produced by the process of the invention from succinic acid and $RRC=CHR$ where R contains 1 to 90 carbon atoms can be converted to an amide to produce a component for a hydrocarbon lubricating oil composition (U.S. Pat. No. 3,200,075). The gamma-butyrolactones produced by the process of the invention from acetic acid and ethylene and from $R_3R_3CH-COOH$ and $R_1R_2-C=C(R)_3$ where H is hydrogen, saturated alkyl, unsaturated alkyl, substituted aryl and unsubstituted aryl may be used to render a polyester or polyether based polyurethane foam hydrophilic (U.S. Pat. No. 3,413,245). The gamma-butyrolactones produced by the process of the invention from halogen acetic acid and ethylene may be used to produce organo-phosphorus compounds having insecticidal activity (U.S. Pat. No. 3,513,175). The gamma-butyrolactones produced by the process of the invention from propionic acid and 5-methyl, pentene-1 may be employed as a flavoring agent (U.S. Pat. No. 3,530,149). The gamma-butyrolactones produced by the process of the invention from $RCH_2COOH$ and $RHC=CHR$ where R is hydrogen or the same or different alkyl group may be used to produce alkyl alcohol and its alkyl derivatives (U.S. Pat. No 3,692,849). The gamma-butyrolactones produced by the process of the invention from acetic acid and $RCH=CHR$ where R is hydrogen or an alkyl, aryl, alkaryl, aralkyl, or cycloalkyl group may be used to produce alpha-carboxylactones which are useful as chemical intermediates for the preparation of the corresponding alpha-methylenelactones, these latter having known utility as fungicides and antibiotics (U.S. Pat. No. 3,697,542).

The process of the invention provides other useful applications which deserve mention because the product involved is of particular interest or because it is convertible to another product of special use. In one case a high molecular weight product having two different functional groups may be formed for use as an antioxidant additive for hydrocarbon lubricants. The antioxidant additives, by addition to the lubricants, prevent oxidative deterioration of the lubricants. A conventional but inconvenient way of making a product of this type is to react a butene polymer with maleic anhydride and an amine to form a structure of the following type,

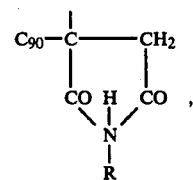

where $C_{90}-$ is the butene polymer moiety. According to the invention, a product of this type may be prepared by reacting a polymer of a four carbon atom olefin, i.e., butene or isobutene, containing about 90 carbon atoms and having terminal unsaturation with manganic acetate to form the lactone,

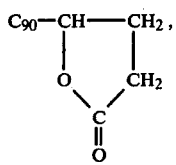

then reacting this with an amine, RNH₂, to form products like

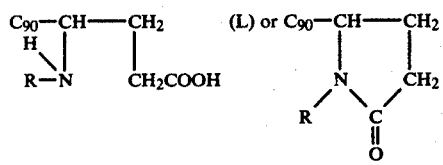

By further treatment of (L) with an amine, RNH₂, there may be formed

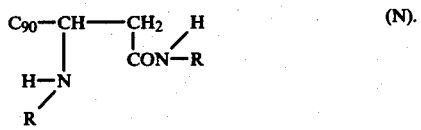

Compounds (M) and (N) are useful as antioxidant additives. Secondary amines can replace the RNH₂.

In another case, antioxidant additives for light hydrocarbon distillates, to prevent oxidative deterioration thereof, may be prepared by reacting propylene tetramer, a terminally unsaturated C12 hydrocarbon, with manganic acetate to form

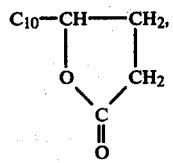

which on treatment with RNH₂ gives the following imide,

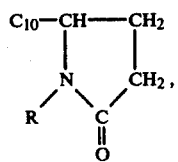

useful for antioxidant use.

An improved adherence in the wax coating of paper can be obtained by taking a C20 to C22 terminal olefin, converting it to a lactone in the manner described, mixing the lactone with the wax, and using the mixture for coating paper by hot melt technique.

The lactone formed from acetic acid and butadiene,

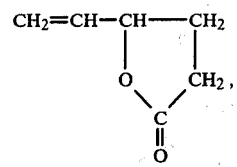

may be reacted either with a polyamine like hexamethylene diamine, or with an acrylate polymer, to form in either case a polymer product for use as a non-metallic detergent in gasoline and other hydrocarbon fractions. The reaction with acrylate polymer involves copolymerization of the carbon-to-carbon double bond of the lactone.

The lactone made from acetic acid and styrene, note Example 7, can be used in the single step sodium acetate fusion reaction to produce alpha-naphthol, a useful intermediate, particularly for making insecticides.

With a polychlorethylene as the unsaturated compound, the resulting lactone is useful to make flame-retarding compounds.

The lactone formed from acetic acid and butene-1, having the formula

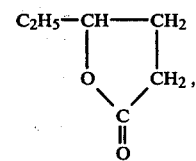

when treated with hot strong acid like polyphosphoric acid, is convertible to cyclohexenone. Similarly, other lactones derived from straight chain 1-olefins may be converted to cycloalkenones, including cyclopentenones and cyclohexenones using polyphosphoric acid, or zinc chloride in acetic acid or acetic anhydride, or stannic chloride in either acetic acid or acetic anhydride.

The lactone from oleic acid and ethylene, i.e., beta-carboxyheptyl-gamma-octyl-butyrolactone may be hydrolyzed with acid to produce 9-carboxymethyl-10-hydroxy-octadecanoic acid, a long dicarboxylic acid having a gamma hydroxy group, which can be used in the manufacture of alkyd resins by condensation with a polyhydric alcohol. Similar products are obtainable, starting with abietic acid, the main constituent of rosin. Of further interest is the capability of the lactone from oleic acid to undergo self-esterification.

Lactones from acetic acid and propylene and butylene are solvents of the "cellosolve" type, i.e., able to dissolve various cellulose derivatives. Lactones from acetic acid and an olefin like decene are useful as lubricant additives to prevent corrosion of ferrous metals.

Starting with heptene-1, one can make the lactone, as described, then hydrogenate it to form n-nonanoic acid, a saturated straight chain monocarboxylic acid, with the carboxyl group on a terminal carbon atom, useful for making jet engine lubricants. In this way, saturated straight chain normal C7, C8, C10, and C11 acids may be made, all of which may be employed to make jet oils and lubricants. Mixtures of these olefins may be used to make mixtures of the acids.

The lactone from acetic acid and heptene-1 can also by hydrogenated over a catalyst like copper chromite to yield a 1,4-diol. Thus,

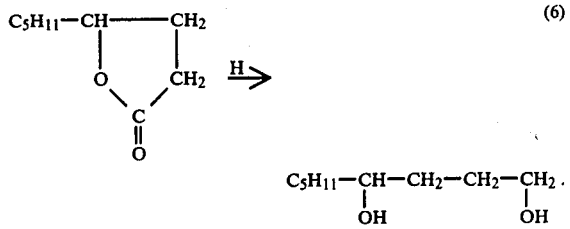   (6)

The product is 1,4-dihydroxynonane. Diols of this kind are of use to make polyesters by condensing them with dibasic acids. Lactones from C3 to C20, C30 or higher olefins may be converted in the foregoing way.

Glutaric acid is obtainable by hydrogenating the lactone from acetic acid and acrylic acid,

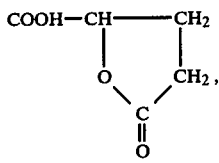

to give the compound, COOHCH$_2$CH$_2$CH$_2$COOH. Lactones from other unsaturated monocarboxylic acids, such as crotonic, also give dicarboxylic acids, which are valuable for polyamide resin formation through condensation with diamines. A dicarboxylic acid may also be formed starting with butadiene, which is converted to a dilactone,

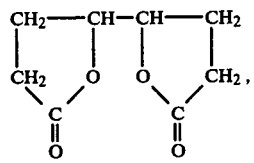

and then hydrogenated to

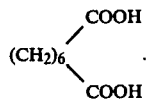

Other conjugated diolefins lead to dicarboxylic acids.

In the light of the foregoing description, the following is claimed.

We claim:

1. A method for the production of a gamma-butyrolactone comprising the step of reacting, at a temperature between 20° C. and 250° C.:

an olefin selected from the group consisting of acyclic monoolefins having 2 to 92 carbon atoms, acyclic diolefins having 3 to 8 carbon atoms, cyclic monoolefins having 5 to 8 carbon atoms and cyclic diolefins having 5 to 8 carbon atoms;
an acid having the formula

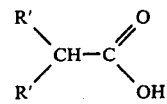

wherein one or both of the R's are selected from the group consisting of hydrogen, straight or branched chain alkyl or alkenyl group having one to ten carbon atoms, cyano and alkyl carboxy having the formula

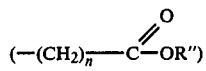

wherein R" is hydrogen or CH$_3$ and n has a value of one to six; and
at least two equivalents per mole of said olefin of an ion of manganese or cerium, the ion being in a valency state higher than its lowest valency state.

2. The method of claim 1 wherein said olefin is an acyclic monoolefin having from 2 to 92 carbon atoms and said acid is acetic acid.

3. The method of claim 1 wherein said step of reaction is conducted in the presence of potassium acetate.

4. The method of claim 1 wherein said ion in a valency state higher than its lowest valency state is an ion of manganese.

5. The method of claim 4 wherein said ion of manganese is in a valency state of +3.

6. The method of claim 4 wherein said ion of manganese is provided by manganic acetate, manganese dioxide or potassium permanganate.

7. The method of claim 1 wherein said ion in a valency state higher than its lowest valency state is cerium in a valency state of four.

8. The method of claim 1 wherein said olefin is an acyclic diolefin having 3 to 8 carbon atoms and said acid is acetic acid or cyanoacetic acid.

9. The method of claim 8 wherein the acyclic diolefin is isoprene.

10. The method of claim 8 wherein the acyclic diolefin is 2,5-dimethylhexadiene-1,5.

11. The method of claim 8 wherein the acyclic diolefin is butadiene.

12. The method of claim 1 wherein said olefin is an acyclic monoolefin having 2 to 10 carbon atoms.

13. The method of claim 1 wherein said olefin is styrene, α-methylstyrene or beta-methyl-styrene.

14. The method of claim 1 wherein said olefin is a hydrocarbon olefin and said acid is acetic acid.

* * * * *